United States Patent
Huang et al.

(10) Patent No.: US 6,918,763 B2
(45) Date of Patent: Jul. 19, 2005

(54) APPARATUS FOR DETECTING THE STABILITY OF A TOOTH IN THE GUM OR AN IMPLANT IN THE BODY

(75) Inventors: Haw-Ming Huang, Taipei (TW); Sheng-Yang Lee, Taipei (TW); Pi-Ying Cheng, Hsinchu (TW); Kuang-Yu Cheng, Taipei (TW); Rong-I Lian, Taoyuan (TW)

(73) Assignee: Miracle One Technology Co., Ltd., Taipei (TW)

( * ) Notice: Subject to any disclaimer, the term of this patent is extended or adjusted under 35 U.S.C. 154(b) by 83 days.

(21) Appl. No.: 10/436,102

(22) Filed: May 13, 2003

(65) Prior Publication Data

US 2004/0096803 A1 May 20, 2004

(30) Foreign Application Priority Data

Nov. 19, 2002 (TW) ........................................ 91133698 A

(51) Int. Cl.⁷ ................................................ A61C 5/00
(52) U.S. Cl. ........................... 433/72; 33/513; 600/552; 600/553; 600/590
(58) Field of Search .................... 433/72, 215; 600/589, 600/590, 552, 553; 33/513

(56) References Cited

U.S. PATENT DOCUMENTS

| | | | | |
|---|---|---|---|---|
| 4,482,324 A | * | 11/1984 | Wohlgemuth | 433/215 |
| 4,819,753 A | * | 4/1989 | Higo et al. | 600/586 |
| 4,881,552 A | * | 11/1989 | Heyman | 600/587 |
| 4,922,898 A | * | 5/1990 | Dunn | 606/85 |
| 5,024,239 A | * | 6/1991 | Rosenstein | 600/587 |
| 5,368,044 A | * | 11/1994 | Cain et al. | 600/552 |
| 5,392,779 A | * | 2/1995 | Meredith et al. | 600/437 |
| 5,437,606 A | * | 8/1995 | Tsukamoto | 601/2 |
| 5,680,874 A | * | 10/1997 | Takuno | 600/587 |
| 5,803,730 A | * | 9/1998 | Khademazad et al. | 433/72 |
| 5,951,292 A | | 9/1999 | Lee et al. | 433/215 |
| 6,712,778 B1 | * | 3/2004 | Jeffcoat et al. | 600/590 |

* cited by examiner

Primary Examiner—Ralph A. Lewis
(74) Attorney, Agent, or Firm—Bacon & Thomas, PLLC

(57) ABSTRACT

An apparatus for detecting the stability of a tooth in the gum or an implant in the body is constructed to include a holder for holding a test object to be examined, an impact device disposed at one side of the holder for striking the test object, causing the test object to produce vibrations, and sensor means disposed at one side of the holder for detecting the vibrations produced by the test object upon the striking of the impact device against the test object.

9 Claims, 9 Drawing Sheets

APPARATUS FOR DETECTING THE STABILITY OF A TOOTH IN THE GUM OR AN IMPLANT IN THE BODY

BACKGROUND OF THE INVENTION

1. Field of the Invention

The present invention relates generally to a detecting apparatus and, more specifically, to an apparatus for detecting the stability of a tooth in the gum or an implant in the body.

2. Description of the Related Art

U.S. Pat. No. 5,951,292, entitled "Method of detecting periodontal disease by detecting the natural frequency of a tooth", issued to the present inventors, teaches a method for detecting the stability of a tooth or an implant such as an artificial tooth. The method involves attaching a vibration detector, e.g. an acceleration gauge or a microphone, to the tooth, causing the tooth to vibrate by means of striking the tooth with a hammer, and then picking up signals corresponding to the vibration of the tooth for processing by a dynamic signal analyzer and a microprocessor using Fourier analysis. The location of the natural frequency of the tooth is determined based on the lowest point in the image mode and the point of contraflexure in the real mode. This method still cannot eliminate human errors because it is to vibrate the tooth or the like in question by striking it manually with an object, for example, a hammer or the like, and detecting vibrations of the tooth induced by impact of the object with the tooth.

SUMMARY OF THE INVENTION

It is the main object of the present invention to provide an apparatus for detecting the stability of a tooth in the gum or an implant in the body, which is compact and precise, and convenient in use.

To achieve this object of the present invention, the apparatus for detecting the stability of a tooth in the gum or an implant in the body comprises a holder for holding a test object, an impact device disposed at one side of the holder for striking the test object, causing the test object to produce vibrations, and sensor means disposed at one side of the holder for detecting the vibrations produced by the test object upon the striking of the impact device against the test object.

DETAILED DESCRIPTION OF THE INVENTION

Figure 1:
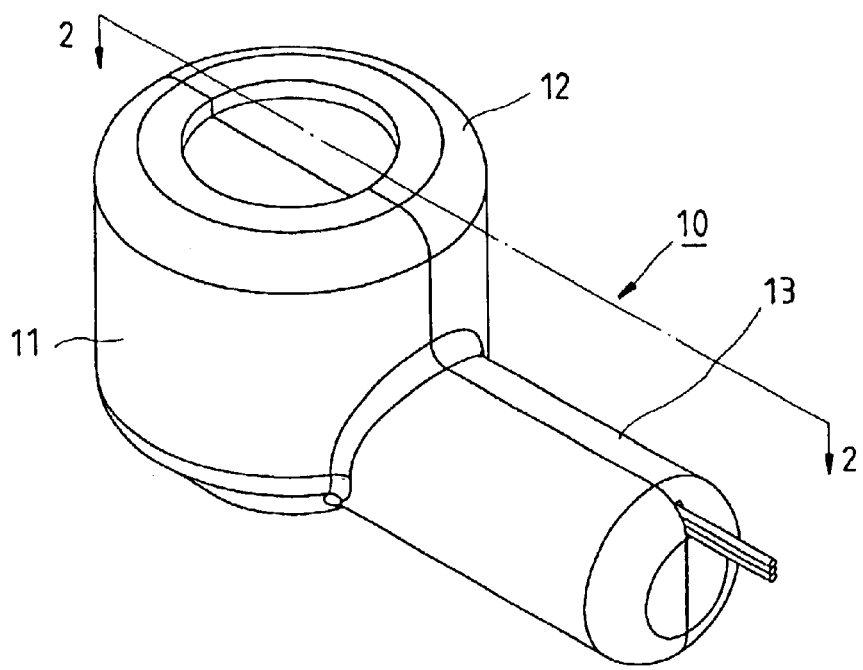
FIG. 1 is a perspective of an apparatus for detecting the stability of a tooth in the gum or an implant in the body according to a first preferred embodiment of the present invention.
Figure 2:
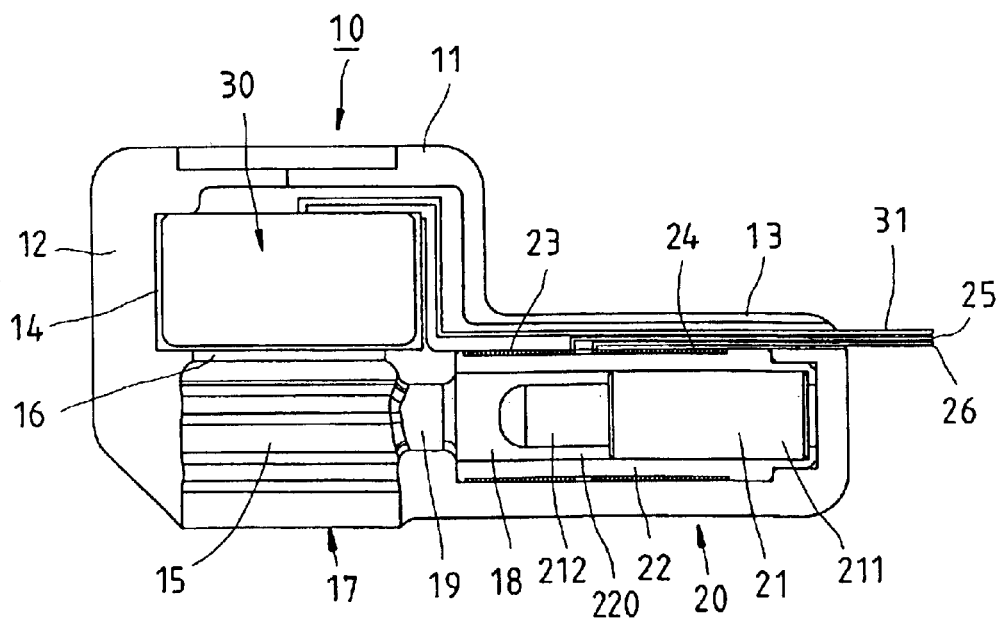
FIG. 2 is a sectional view taken along line 2—2 of FIG. 1.
Figure 3:
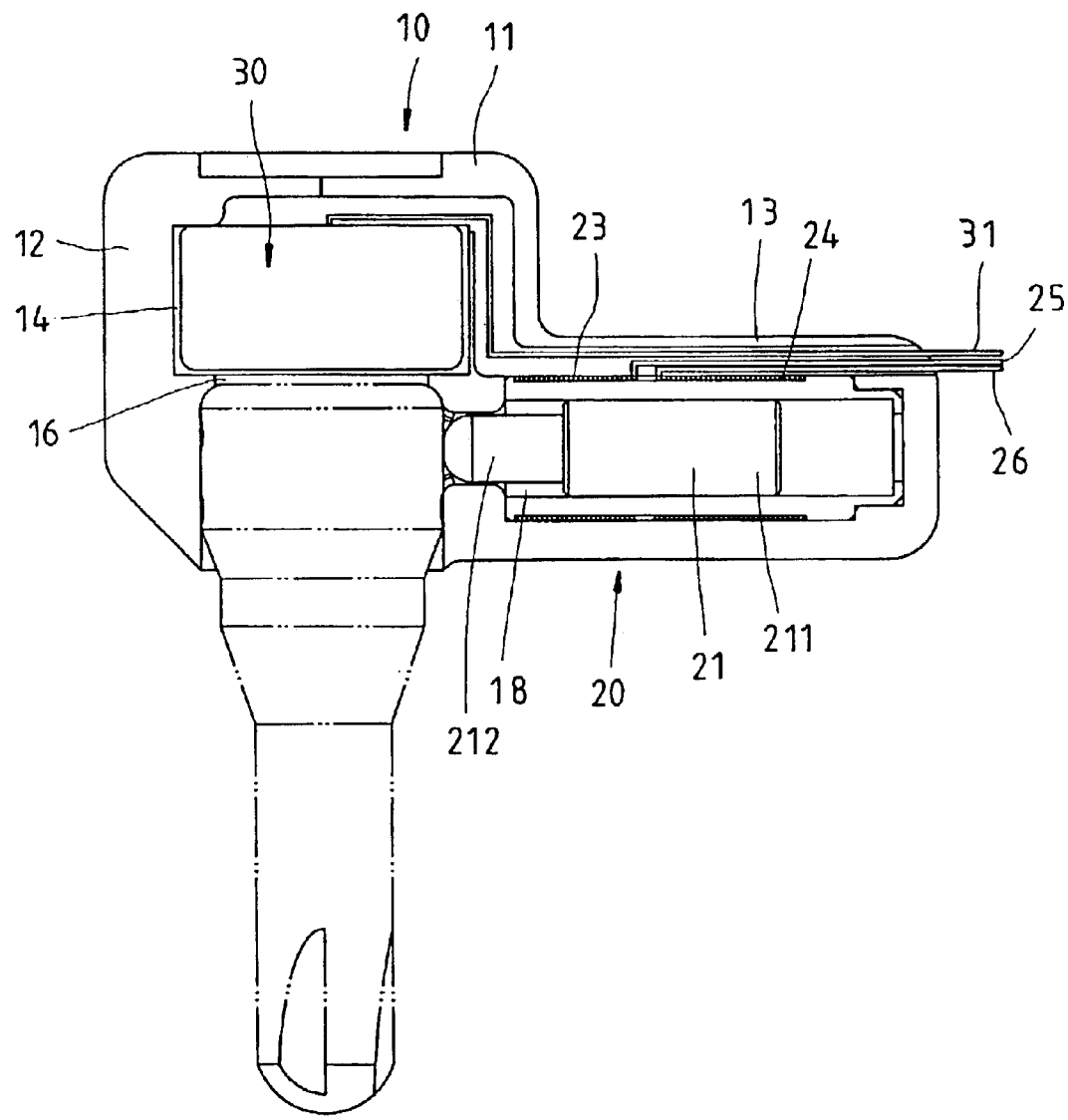
FIG. 3 is a schematic view of the first preferred embodiment of the present invention showing the impact member stroke the test object.

Referring to FIGS. 1~3, an apparatus for detecting the stability of a tooth in the gum or an implant in the body in accordance with the first preferred embodiment, referenced by 10, is shown comprised of a shell 11, an impact device 20, and sensor means 30.

The shell 11 is molded from plastics, having a cylindrical body portion 12, and an impact device holder portion 13 perpendicularly extended from the cylindrical body portion 12 at one side. The cylindrical body portion 12 defines a top storage chamber 14, a bottom receiving chamber 15, and a vertical through hole 16 in communication between the top storage chamber 14 and the bottom receiving chamber 15. The bottom receiving chamber 15 has a bottom open side forming a test object holder 17. The impact device holder portion 13 defines an elongated chamber 18 and a horizontal through hole 19 in communication between the elongated chamber 18 and the bottom receiving chamber 15.

The impact device 20 is comprised of an impact member 21 made of iron or magnetically inductive metal, a tube 22, a driving coil 23, a return coil 24, and electrically conductive wires 25 and 26. The impact member 21 is movably mounted in the elongated chamber 18, and moved between a start position remote from the object to be inspected (see FIG. 2) and an impact position to strike the object to be inspected (see FIG. 3). According to this embodiment, the impact member 21 has a body 211 and a head 212 forwardly extended from the body 211. The body 211 has an outer diameter greater than the horizontal through hole 19. The head 212 has an outer diameter relatively smaller than the body 211, and can pass through the horizontal through hole 19 to strike the test object in the receiving chamber 15. The tube 22 is fixedly mounted in the elongated chamber 18. The body 211 of the impact member 21 is fastened moveably with the axial hole 220 of the tube 22. The driving coil 23 is wound round the tube 22 near one end adjacent to the horizontal through hole 19. When electrically connected, the driving coil 23 induces a magnetic force to attract the impact member 21 to move from the start position shown in FIG. 2 to the impact position shown in FIG. 3. The return coil 24 is wound round the tube 22 near the other end remote from the through hole 19. When electrically connected, the return coil 24 induces a magnetic force to attract the impact member 21 to move from the impact position shown in FIG. 3 to the start position shown in FIG. 2. The conductive wires 25 and 26 are respectively extended from the driving coil 23 and the return coil 24 to the outside of the shell 11 for connection to power source.

According to this embodiment, the sensor means 30 is a miniature sensing element, i.e. microphone, mounted inside the storage chamber 14 and aimed at the vertical through hole 16, and adapted to detect vibrations of the test object and to output a signal indicative of the vibrations of the test object through a conductive wire 31. An acceleration gauge or vibration wave detection element may be used for the sensing element instead of a miniature microphone.

Figure 8:
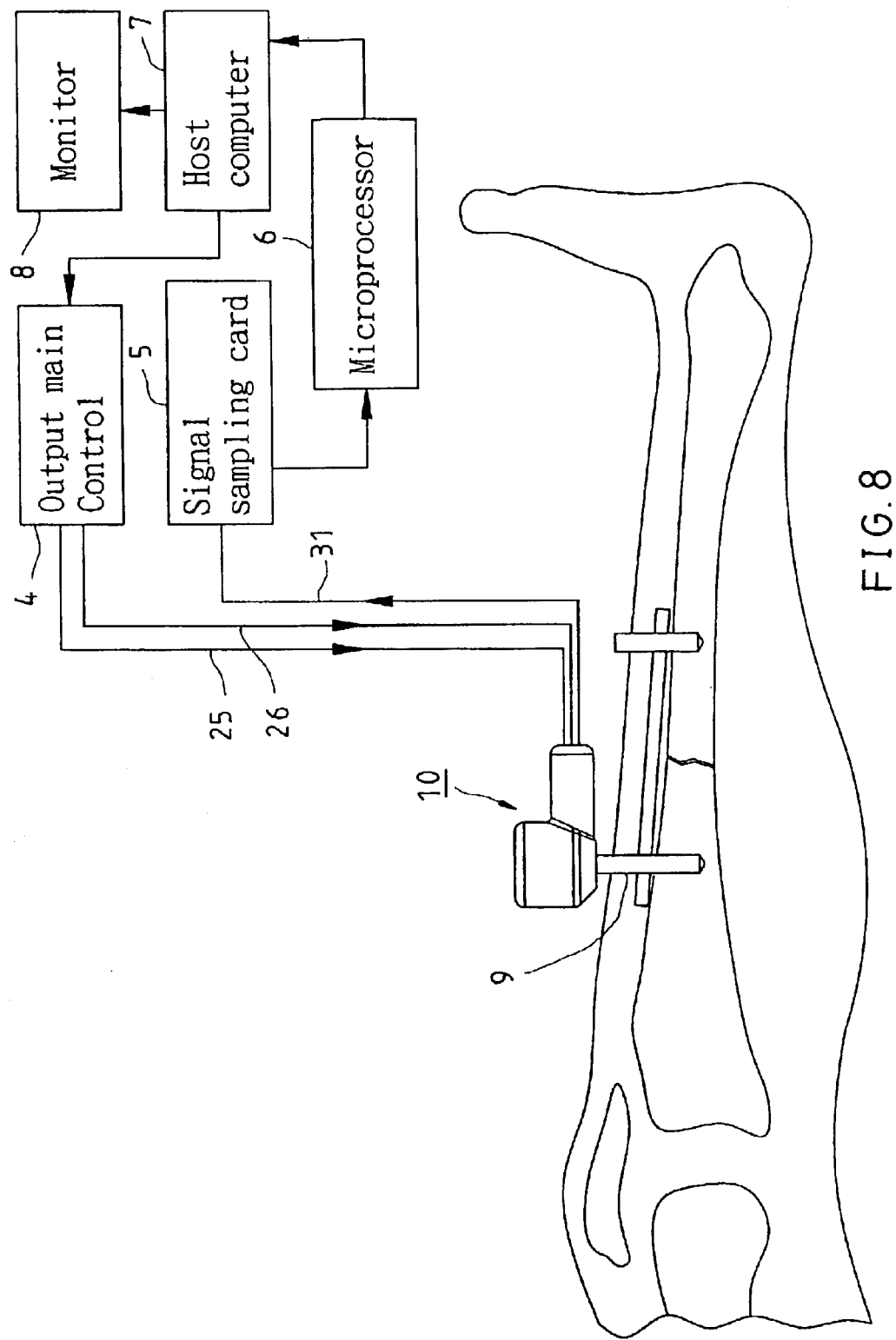
FIG. 8 is an applied view of the first preferred embodiment of the present invention, showing an inspection for the stability of an implant (bone nail in a patient's leg).

The apparatus 10 must be used with other equipment. FIG. 8 shows the use of the apparatus 10 to detect the stability of a bone nail 9 in which the reference number 4 indicates an output main control; the reference number 5 indicates a signal sampling card; the reference number 6 indicates a microprocessor; the reference number 7 indicates a host computer; the reference number 8 indicates a monitor. At first, the test object is inserted into the receiving chamber 15 of the apparatus 10, and then the conductive wires 25 and 26 are respectively connected to the output main control 4 and the conductive wire 31 is connected to the signal sampling card 5. During operation, the output main control 4 outputs an impulse current to the driving coil 23 through the conductive wire 25, causing the driving coil 23 to induce a magnetic field, which drives the impact member 21 to move from the start position to the impact position and to strike the test object with the head 212. Thereafter, the output main control 4 outputs an impulse current to the return coil 24 through the conductive wire 26, causing the return coil 24 to induce a magnetic field, which drives the impact member 21 to move from the impact position to the start position, preventing a repeat striking. The vibration signal produced upon striking of the impact member 21 against the test object is picked up by the microphone 30 and transmitted to the signal sampling card 5 through the conductive wire 31, and then transmitted to the microprocessor 6 for performing a frequency domain analysis. The analyzed data is then transmitted by the microprocessor 6 to the host computer 7 for judgment, and then outputted to the monitor 8 for display. In order to eliminate error, the striking times can be preset by the host computer. Immediately after transmission of the analyzed data by the microprocessor 6 to the host computer 7, the output main control 4 can output an impulse current, and the aforesaid procedure is repeated.

Figure 4:
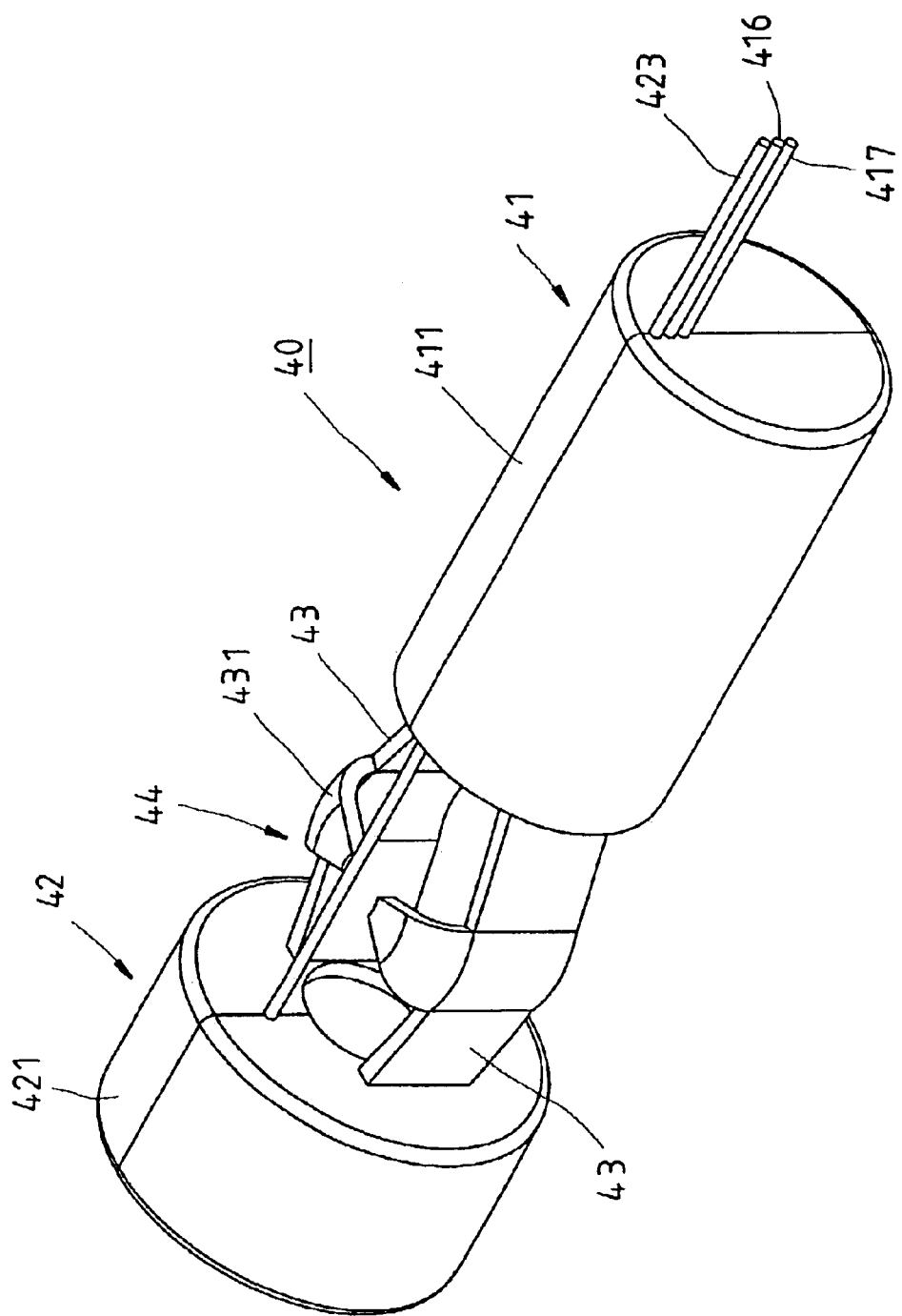
FIG. 4 is a perspective view of an apparatus for detecting the stability of a tooth in the gum or an implant in the body according to, a second preferred embodiment of the present invention.
Figure 5:
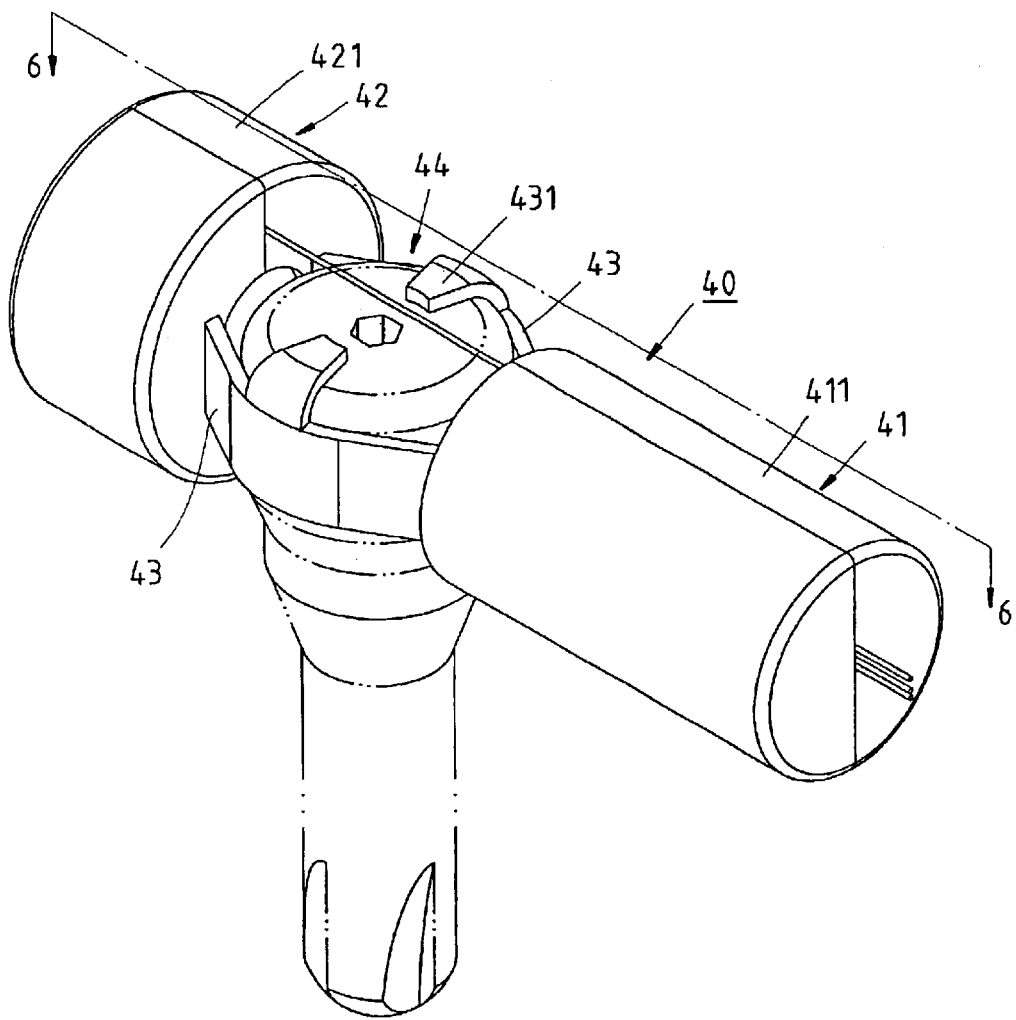
FIG. 5 is a schematic drawing showing a status of use of the second preferred embodiment of the present invention.
Figure 6:
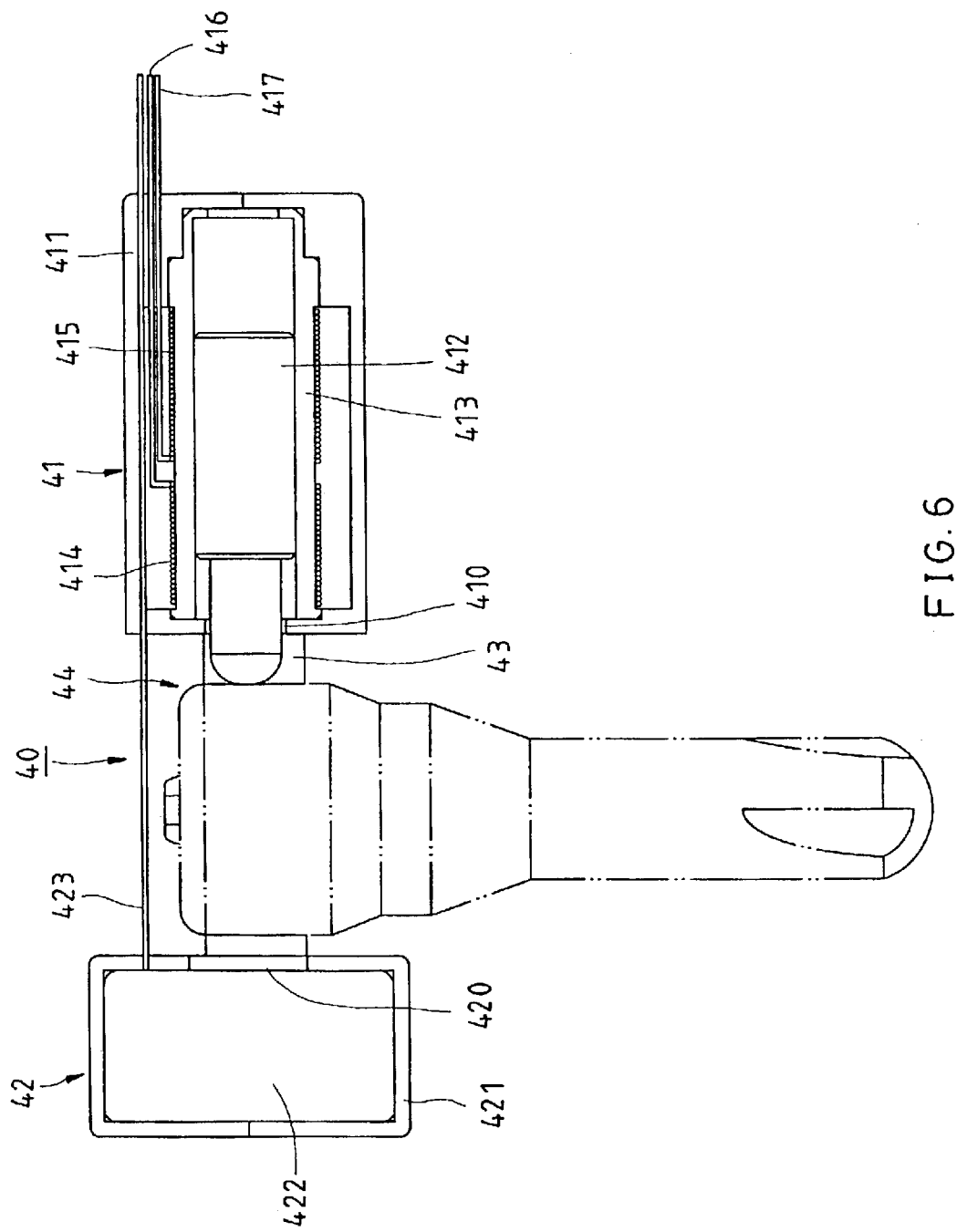
FIG. 6 is a sectional view taken along line 6—6 of FIG. 5.

FIGS. 4–6 show the second preferred embodiment of the present invention. According to this embodiment, the apparatus 40 also comprises an impact device 41, and sensor means 42. The impact device 41 and the sensor means 42 have a respective shell 411 or 421. Two flexible clamping plates 43 are connected between the shells 411 and 421, defining therebetween a test object holder 44. The flexible clamping plates 43 have a respective protruded top stop portion 431 extending toward each other. The clamping plates 43 can be made from resilient metal, for example, memory alloy, plastics, or the combination of resilient metal and plastics. As illustrated in FIG. 6, the sensing element, i.e. microphone 422, is mounted in the shell 421, having a conductive wire 423 for signal output; the impact member 412, the tube 413, the driving coil 414, the return coil 415, and the conductive wires 416 and 417 are mounted in the shell 411 of the impact device 41. The shell 411 of the impact device 41 has a through hole 410 in communication with the test object holder 44 for the passing of the impact member 412 to strike the test object. The shell 421 of the sensor means 42 has a through hole 420 in communication with the test object holder 44 for enabling the microphone 422 to pick up vibrations from the test object. The dotted line shown in FIG. 6 as well FIG. 7 indicates an artificial tooth.

Figure 7:
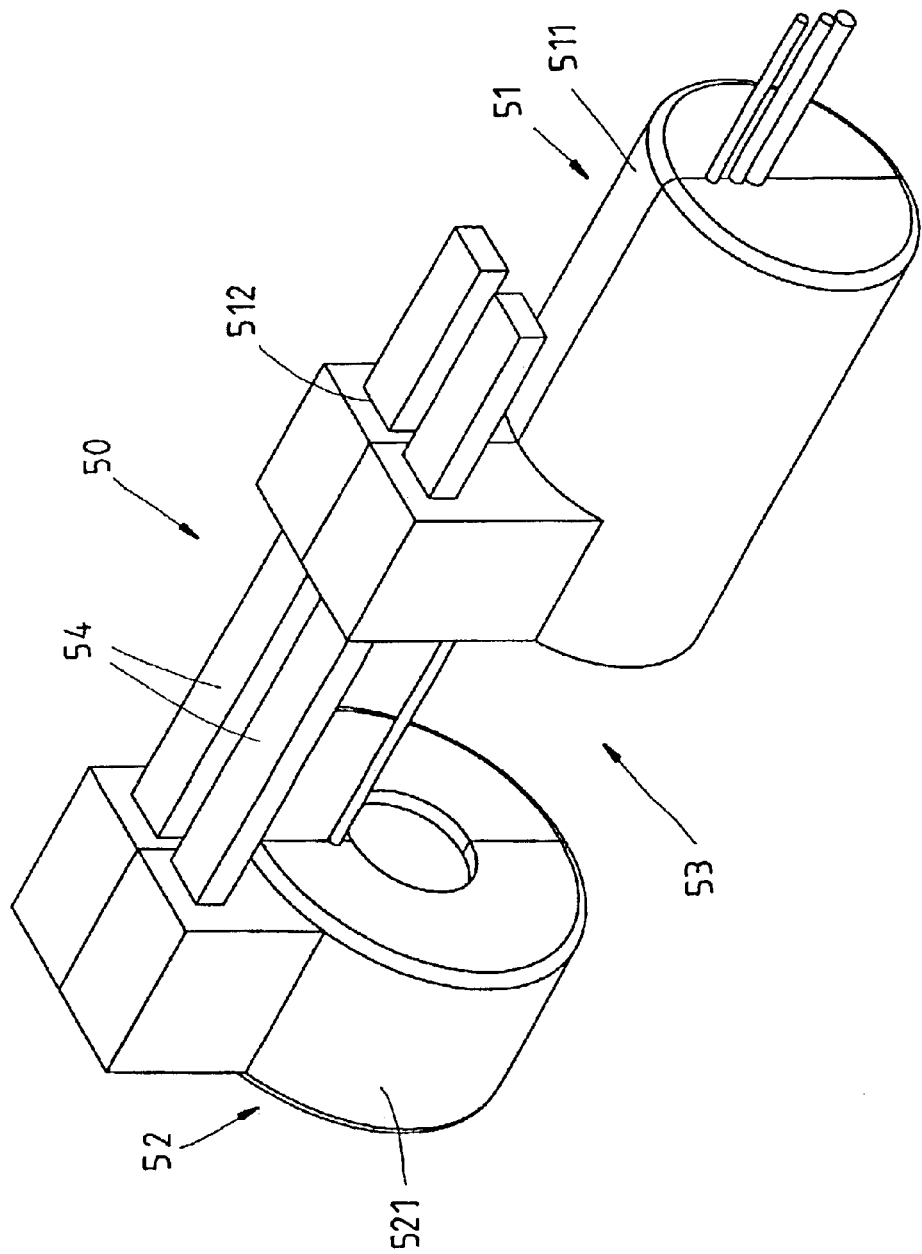
FIG. 7 is a perspective view of an apparatus for detecting the stability of a tooth in the gum or an implant in the body according to a third preferred embodiment of the present invention.

FIG. 7 shows an apparatus 50 for detecting the stability of a tooth in the gum or an implant in the body in accordance with the third preferred embodiment. According to this embodiment, the apparatus 50 comprises an impact device 51, sensor means 52, and a test object holder 53 defined between the impact device and the sensor means. The shell 521 of the sensor means 52 has two guide rails 54. The shell 511 of the impact device 51 has two through holes 512, which receive the guide rails 54 respectively. By means of moving the shell 511 of the impact device 51 along the guide rails 54, the test object holder 53 is adjusted to hold down or release the test object.

Figure 9:
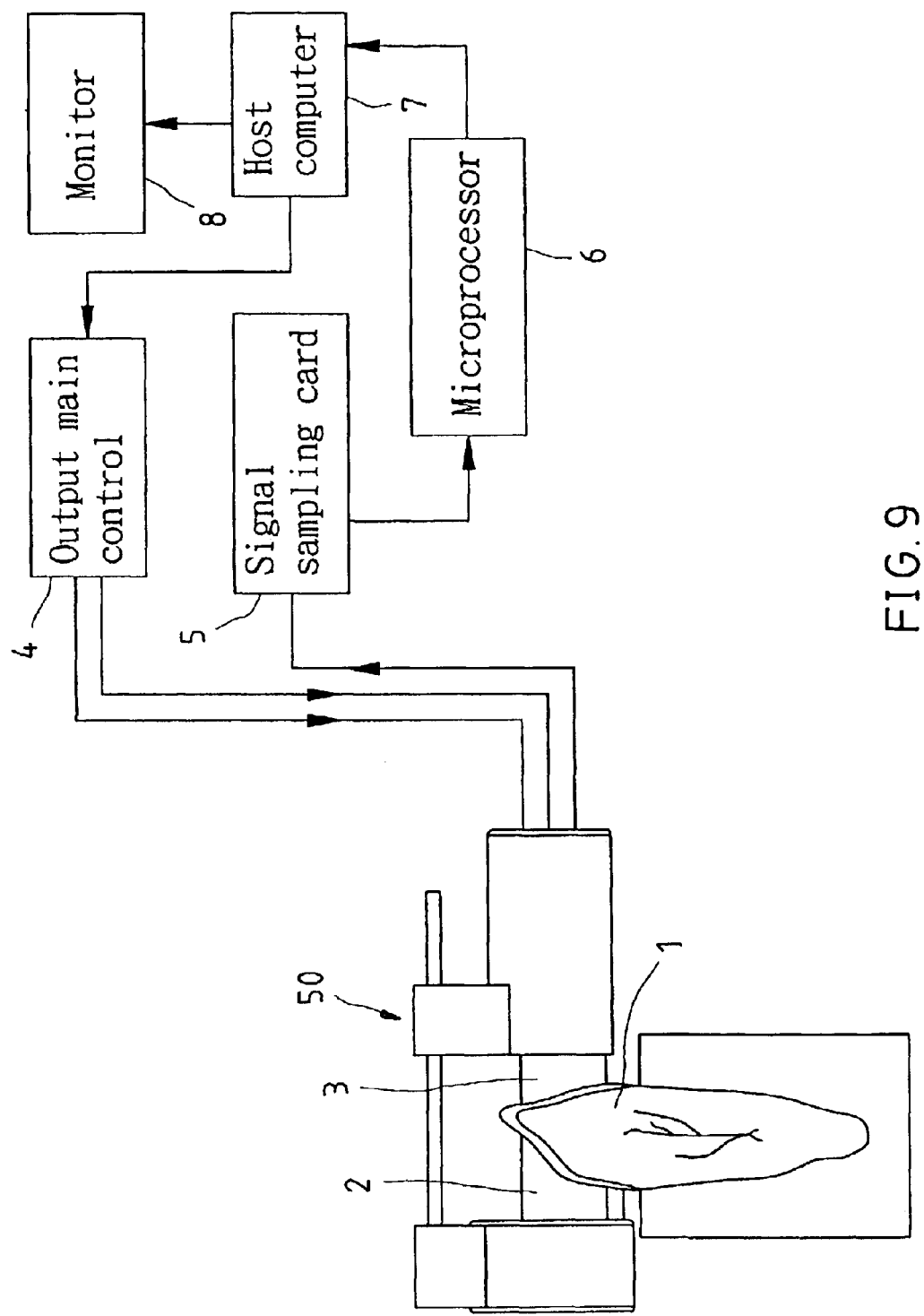
FIG. 9 is an applied view of the third preferred embodiment of the present invention, showing an inspection for the stability of a tooth in the gum.

FIG. 9 is an applied view of the third embodiment according to the present invention. The equipment used with the apparatus 50 is same as that shown in FIG. 7. The reference numbers 2 and 3 indicate clamping elements holding down a tooth 1.

Figure 10:
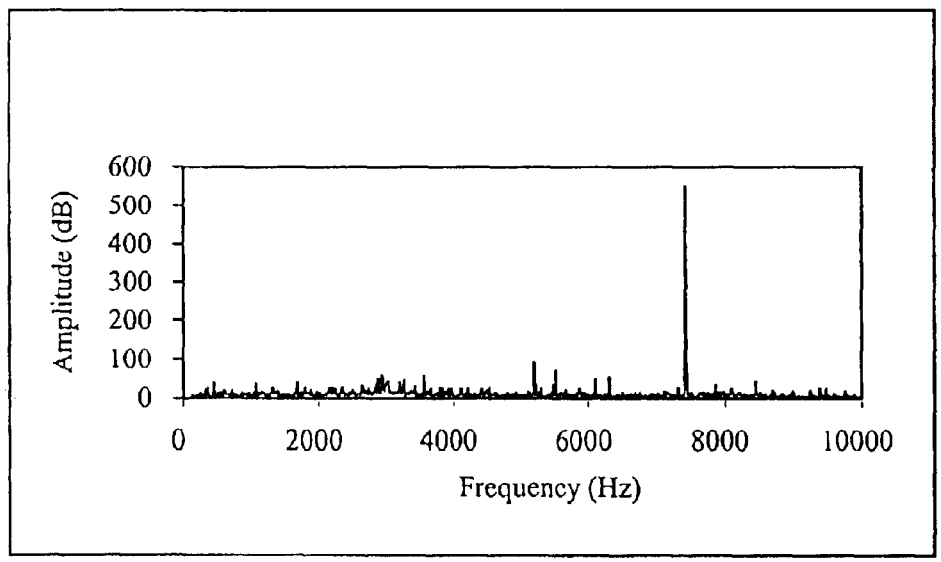
FIG. 10 is an amplitude-frequency chart obtained from an implant through the apparatus of the present invention.

FIG. 10 is an amplitude-frequency chart obtained from an implant through the apparatus of the present invention, in which the horizontal axis is the frequency, the vertical axis is the amplitude. The frequency corresponding to the maximum amplitude is the natural frequency of the test object, which is indicative of the health of the gums supporting the tooth or the tissues supporting the implant.

Figure 11:
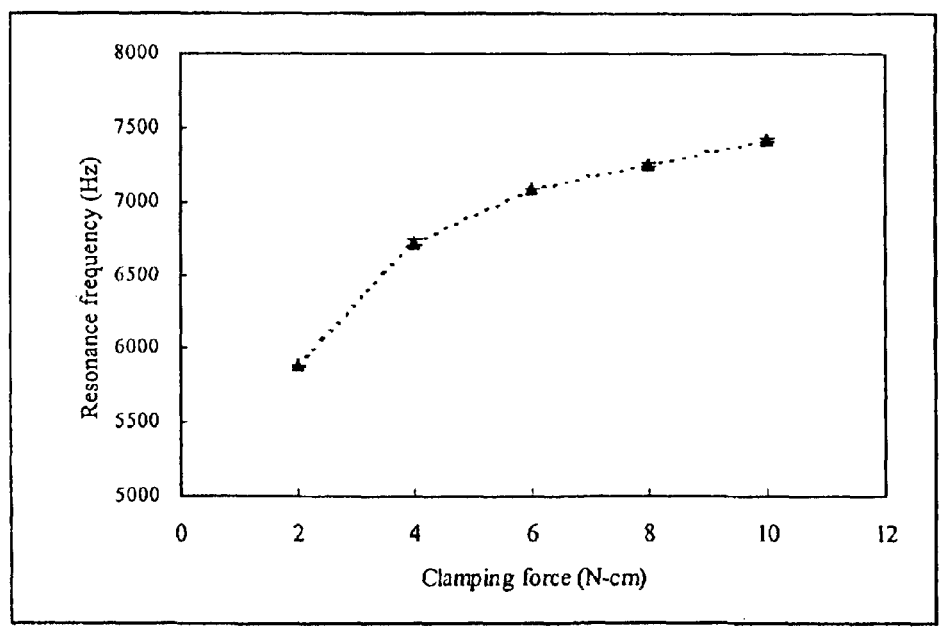
FIG. 11 is a resonance frequency-clamping force chart according to the present invention.

FIG. 11 is a resonance frequency-clamping force chart according to the present invention, in which the horizontal axis is the clamping force received by the test object, i.e. the tooth, implant, artificial tooth, etc., and the vertical axis is the resonance frequency. When the detected natural frequency of the implant or the artificial tooth is increased, it means that the implant-bone integrated strength, i.e. the degree of the osseointegration, of the implant or the artificial tooth is increased. When the detected natural frequency reaches a stable value, the osseointegration of the implant or the artificial tooth is complete. Accordingly, the stability of the implant or the tooth can be detected.

As indicated above, the invention uses an impact member to strike against the test object for measuring the stability of the test object. Because this method is free from the applied force from the operator, it eliminates human errors. Further, because the apparatus is not an intrusive or destructive test apparatus, it is suitable for long-term tracing examination, and practical for use in hospitals as well as at home.

What is claimed is:

1. An apparatus for detecting the stability of a tooth in the gum or an implant in the body comprising:

a holder for holding a test object;

an impact device disposed at one side of said holder for striding the test object, causing the test object to produce vibrations; and sensor means disposed at one side of said holder for detecting the vibrations produced by the test object upon the striking of said impact device against the test object, wherein said impact device comprises a shell having an elongated chamber with an opening to be aimed at the test object, a magnetically inductive impact member mounted inside said elongated chamber and movable between a start position remote form the test object and an impact position to strike the test object, and a driving coil for producing a magnetic force to attract said impact member to move from said start position to said impact position when electrically connected.

2. The apparatus for detecting the stability of a tooth in the gum or an implant in the body as claimed in claim 1, wherein said impact device further comprises return means for moving said impact member from said impact position to said start position.

3. The apparatus for detecting the stability of a tooth in the gum or an implant in the body as claimed in claim 2, wherein said return means is a return coil for producing a magnetic force to attract said impact member to move from said impact position to said start position when electrically connected.

4. The apparatus for detecting the stability of a tooth in the gum or an implant in the body as claimed in claim 1, wherein said sensor means comprises a shell and a sensing element mounted in the shell.

5. The apparatus for detecting the stability of a tooth in the gum or an implant in the body as claimed in claim 4, wherein said sensing element is a microphone.

6. The apparatus for detecting the stability of a tooth in the gum or an implant in the body as claimed in claim 4, wherein said sensing element is an acceleration gauge.

7. An apparatus for detecting the stability of a tooth in the gum or an implant in the body comprising:

a holder for holding a test object;

an impact device disposed at one side of said holder for striding the test object, causing the test object to produce vibrations;

sensor means disposed at one side of said holder for detecting the vibrations produced by the test object upon the striking of said impact device against the test object, and a shell having a body portion and an impact device holder portion, said body portion being provided with a storage chamber, which receives said sensor means, a receiving chamber adapted to accommodate the test object, and a through hole in communication between said storage chamber and said receiving chamber, said receiving chamber having a bottom open side forming said holder, said impact device holder portion being provided with an elongated chamber for holding said impact device and a through hole in communication between said elongated chamber and said receiving chamber.

8. An apparatus for detecting the stability of a tooth in the gum or an implant in the body comprising:

a holder for holding a test object;

an impact device disposed at one side of said holder for striding the test object, causing the test object to produce vibrations; and sensor means disposed at one side of said holder for detecting the vibrations produced by the test object upon the striking of said impact device against the test object, wherein said impact device and said sensor means are respectively provided with a shell; the apparatus further comprising two flexible clamping plates connected between said shells and defining therebetween said holder.

9. An apparatus for detecting the stability of a tooth in the gum or an implant in the body comprising:

a holder for holding a test object;

an impact device disposed at one side of said holder for striding the test object, causing the test object to produce vibrations;

sensor means disposed at one side of said holder for detecting the vibrations produced by the test object upon the striking of said impact device against the test object, wherein said sensor means provided with a shell; said shells defining said holder therebetween; one of the shells being provided with at least one through hole and the other of the shells being provided with at least one guide rail slidably inserted through the through holes for enabling said shells to be moved relative to each other to adjust the pitch of said holder.

* * * * *